(12) United States Patent
Suzuki et al.

(10) Patent No.: US 9,810,647 B2
(45) Date of Patent: Nov. 7, 2017

(54) ENCLOSED X-RAY IMAGING SYSTEM (71) Applicant: NIKON METROLOGY NV, Leuven (BE)

(72) Inventors: Kazuaki Suzuki, Berkhamsted Hertfordshire (GB); Daniel Hilton, Aylesbury Hertfordshire (GB)

(73) Assignee: NIKO METROLOGY NV, Leuven (BE)

( * ) Notice: Subject to any disclaimer, the term of this patent is extended or adjusted under 35 U.S.C. 154(b) by 56 days.

(21) Appl. No.: 14/890,394

(22) PCT Filed: May 12, 2014

(86) PCT No.: PCT/EP2014/059619
§ 371 (c)(1),
(2) Date: Nov. 10, 2015

(87) PCT Pub. No.: WO2014/184127
PCT Pub. Date: Nov. 20, 2014

(65) Prior Publication Data
US 2016/0109389 A1 Apr. 21, 2016

(30) Foreign Application Priority Data
May 13, 2013 (GB) .................. 1308597.2

(51) Int. Cl.
*G01N 23/04* (2006.01)

(52) U.S. Cl.
CPC ... *G01N 23/046* (2013.01); *G01N 2223/1016* (2013.01); *G01N 2223/31* (2013.01); *G01N 2223/419* (2013.01)

(58) Field of Classification Search
CPC ....... A61B 6/032; A61B 6/035; A61B 6/5205; G01N 23/046; G06T 11/006

(Continued)

(56) References Cited

U.S. PATENT DOCUMENTS

| 4,969,167 A | 11/1990 | Zupancic et al. |
| 5,848,122 A | 12/1998 | Kurtz |
| 2013/0083896 A1 | 4/2013 | Watanabe |

FOREIGN PATENT DOCUMENTS

| JP | 62115086 U | 7/1987 |
| JP | 08131569 A | 5/1996 |

(Continued)

OTHER PUBLICATIONS

International Search Report and Written Opinion for Application No. PCT/EP2014/059619 dated Jul. 4, 2014, 9 pages.

(Continued)

*Primary Examiner* — Don Wong
(74) *Attorney, Agent, or Firm* — Andrew M. Calderon; Roberts Mlotkowski Safran Cole & Calderon P.C.

(57) ABSTRACT

According to the present disclosure, there is provided an x-ray imaging system, comprising: an x-ray source; an x-ray detector; a sample mount for mounting a sample in a beam path between the x-ray source and the x-ray detector; an enclosure enclosing at least the sample mount in an interior of the enclosure; and a climate control system for regulating the climate inside the enclosure, wherein: the enclosure has an aperture for enabling access to at least the sample mount from outside the enclosure; the enclosure is provided with a door operable between an open position in which the aperture is open and a closed position in which the aperture is closed by the door; and the climate control system is operable to provide a positive pressure differential between the interior of the enclosure and an exterior of the enclosure such that the interior of the enclosure is maintained at a higher pressure than the exterior of the enclosure when the door is open. Such a system is able to better regulate the temperature inside the enclosure even when the door is opened.

27 Claims, 6 Drawing Sheets

(58) Field of Classification Search
USPC .......................................... 378/57, 4, 207, 20
See application file for complete search history.

(56) References Cited

FOREIGN PATENT DOCUMENTS

| JP | 2003100620 A | 4/2003 |
|----|---|---|
| JP | 2009139314 A | 6/2009 |
| WO | 9919714 A1 | 4/1999 |
| WO | 0023795 A1 | 4/2000 |
| WO | 0033058 A2 | 6/2000 |
| WO | WO-0033058 A2 | 6/2000 |
| WO | WO-2010124868 | 11/2010 |
| WO | 2014184127 | 11/2014 |

OTHER PUBLICATIONS

Unknown, "National Ignition Facility—User Guide", Oct. 1, 2012, XP055125293, California, Retreived from the Internet on Jun. 26, 2014, pp. 85-91.
Search Report for GB Application No. GB1308597.2, dated Oct. 16, 2013; 2 Pages.
Search Report for GB Application No. GB1308597.2 dated Feb. 10, 2016; 5 Pages.
Japanese Office Action for the related Application No. 2016-513313 dated Oct. 25, 2016, dated Oct. 31, 2016, 6 pages.

ENCLOSED X-RAY IMAGING SYSTEM

TECHNICAL FIELD

The present invention relates to an x-ray imaging system, and particularly to an enclosed x-ray imaging system which is able to provide a positive pressure differential between an interior of the enclosure and an exterior of the enclosure.

BACKGROUND ART

X-ray imaging is a valuable diagnostic tool for analysing the interior structure of a sample. In an x-ray imaging system, a sample is placed between an x-ray source and an x-ray detector, and the detector is irradiated with x-rays from the source via the sample. The intensity of the x-rays received at the detector via the sample depends on the degree to which the portions of the sample through which the x-ray beam passes attenuate the x-ray beam. Analysis of the detected x-rays is therefore able to provide information about the internal structure of the sample.

In traditional two-dimensional x-ray imaging, a single projective image of a sample is acquired by placing the sample between an x-ray source and a two-dimensional detector, or a photographic plate, to measure a single projection of the sample. If the dimensions of the source are small compared with the distance to the sample, each point on the detector receives x-ray radiation which has passed through the sample at a well-defined angle from the source. While useful in some circumstances, this technique provides only limited information about the internal structure of the sample, since radiodense (relatively opaque to x-ray) features of the sample will tend to occlude radiolucent (relatively translucent to x-ray) features, and information about the sample in the direction of the beam centreline, that is, depth information, is lacking.

In computed tomography (CT), a series of x-ray projections are acquired over a range of angles about one or more predetermined axes of the sample. This can be achieved by holding source and detector fixed in a predetermined spatial relationship and rotating the sample relative to the source and detector, or by holding the sample fixed and rotating the source and detector in a predetermined spatial relationship about the sample. At each angular step, one x-ray projection of the series is acquired. Mathematical reconstruction using each of the projections in the acquired series allows a volumetric map of the radiodensity of the interior of the sample to be obtained. Such a reconstruction can provide valuable diagnostic information about the interior of the sample.

However, in computed tomography, the acquisition process may involve acquiring projections at a series of angles about the sample with increments between angles in the series of as little as 0.1 or 0.05 degree. The smaller the angular interval between projections, the better the resolution of the volumetric reconstruction is. Also, the signal-to-noise in each of the acquired projections is generally improved with longer exposures for each projection. Therefore, a single computed tomography acquisition series can be very lengthy, if it is important to obtain either or both of high resolution and good signal-to-noise.

During the series acquisition, changes in, for example, the size and shape of the sample, the relative alignment of source and detector, or the relative separation of source, detector, and sample can result in blurring of the reconstructed volume map and a consequent loss of resolution. It is thus of importance to ensure that, aside from the intended incremental change in angle of the x-ray projection about the sample, all other dimensions and spatial relationships of the sample and the x-ray imaging system remain constant throughout the imaging process.

Therefore, in high-resolution imaging systems, it is important that the dimensional stability of the whole system, including the dimensions of the source, the detector and the sample, as well as their relative separations and orientations, is preserved even over long timescales.

It is conventional that the x-ray imaging system is contained within an enclosure which is opaque to x-rays. This allows an operator to conveniently operate the x-ray imaging apparatus, as well to make appropriate adjustments to the sample or exchanges of one sample with another, between accumulations, without being subject to the x-ray radiation. When such an enclosure is in a closed state, the temperature inside the enclosure may be well-controlled. Therefore, dimensional stability of both the sample and the source-detector system, which comprises the source and detector arranged in a predetermined spatial relationship, may be high. Specifically, the dimensional stability of the source-detector system can include the stability of the alignment between the source and the detector, the stability of the spacing between the source and the detector, and the stability of the dimensions of individual components of each of the source and the detector, at least.

However, when the enclosure is opened, either to adjust the position of the sample or to replace the sample with another sample, the temperature of the air inside the enclosure can change depending on the temperature of the air outside the enclosure. As a consequence, thermal expansion, or contraction of the sample and of the source-detector system can occur.

Once the enclosure is closed, the temperature inside the enclosure will return to a normal operating condition over a period of time. During this period of time, any x-ray accumulation will tend to suffer blurring defects due to thermal expansion or contraction of the source-detector system, of the sample, or of both.

Therefore, it is customary to wait for the enclosure and sample temperatures to stabilise after the enclosure is closed and before the accumulation of imaging data begins. This limits the rate at which a series of different samples may be imaged, and also lengthens the imaging process if, for example, the position or attitude of the sample requires adjustment between exposures. In particular, to obtain a particular view of a portion of a sample, an operator may need to manually adjust the position of the sample several times, acquiring an image at each time, before the desired view is obtained. The need to allow time for the temperature inside the enclosure to stabilise slows this procedure.

There is therefore a need for an enclosed x-ray imaging system which is better able to maintain the internal temperature even when the enclosure is opened.

SUMMARY

According to the present disclosure, there is provided an x-ray imaging system, comprising: an x-ray source; an x-ray detector; a sample mount for mounting a sample in a beam path between the x-ray source and the x-ray detector; an enclosure enclosing at least the sample mount in an interior of the enclosure; and a climate control system for regulating the climate inside the enclosure, wherein: the enclosure has an aperture for enabling access to at least the sample mount from outside the enclosure; the enclosure is provided with a door operable between an open position in which the aperture is open and a closed position in which the aperture is closed by the door; and the climate control system is operable to provide a positive pressure differential between the interior of the enclosure and an exterior of the enclosure such that the interior of the enclosure is maintained at a higher pressure than the exterior of the enclosure when the door is open.

In some embodiments, the climate control system comprises an air conditioner arranged to regulate at least the temperature of the air inside the enclosure.

In some embodiments, the climate control system comprises a blower arranged to draw air from outside the enclosure and to supply it to the interior of the enclosure to provide the positive pressure differential.

In some embodiments, the air conditioner comprises a temperature regulator for regulating the temperature of the air supplied from outside the enclosure to the interior of the enclosure.

In some embodiments, the climate control system comprises an air flow regulator for regulating the flow of the air supplied by the blower from outside the enclosure to the interior of the enclosure.

In some embodiments, the temperature regulator comprises a further air conditioner arranged to regulate the temperature inside the enclosure.

In some embodiments, the climate control system is configured to detect a condition in which the door is open and to provide the positive pressure differential when the door is open.

In some embodiments, the climate control system is configured to detect a condition when a temperature inside the enclosure either exceeds or drops below a predetermined threshold and to provide the positive pressure differential when the temperature exceeds or drops below the predetermined threshold.

In some embodiments, the climate control system is configured to detect a condition when a temperature inside the enclosure either exceeds or drops below a predetermined threshold and to adjust the temperature of the air supplied from outside the enclosure to the interior of the enclosure when the temperature exceeds or drops below the predetermined threshold.

In some embodiments, the enclosure comprises a flexible curtain arranged to cover the aperture when the door is open.

In some embodiments, the curtain is transparent.

In some embodiments, the enclosure comprises an air curtain arranged to operate across the aperture to reduce air flow through the aperture when the door is open.

In some embodiments, the air curtain is configured to operate when the door is open.

In some embodiments, the aperture is less than 1 m² in area.

In some embodiments, the climate control system comprises a temperature sensor inside the enclosure and arranged to provide an interior temperature measurement.

In some embodiments, the climate control system comprises a plurality of temperature sensors inside the enclosure each arranged to provide a local interior temperature measurement at one location in the enclosure, and wherein the climate control system is arranged to determine an interior temperature measurement on the basis of the local interior temperature measurements.

In some embodiments, the climate control system comprises a pressure sensor inside the enclosure and arranged to provide an interior pressure measurement.

In some embodiments, the climate control system comprises a pressure sensor outside the enclosure and arranged to provide an exterior pressure measurement.

In some embodiments, the climate control system comprises a differential pressure sensor arranged to provide a differential pressure measurement between the interior and the exterior of the enclosure.

In some embodiments, the enclosure also encloses the x-r source, the x-ray detector, or both.

In some embodiments, the air conditioner is arranged to provide a positive differential pressure of between 1 and 10 mBar when the door is open.

In some embodiments, the mount, source and detector are together configured for computed tomography imaging such that the source and detector are relatively rotatable with reference to the sample mount.

In some embodiments, the system further comprises a controller adapted to control the relative rotation of source and detector with reference to the sample mount.

In some embodiments, the system further comprises a memory adapted to record a series of x-ray images acquired at a series of angles in the relative rotation of source and detector with reference to the sample mount.

In some embodiments, the x-ray system comprises a tomography reconstruction unit, which is adapted to apply mathematical transformations to the series of x-ray images to calculate a volumetric density map.

In some embodiments, the source and detector are arranged to be fixed relative to the enclosure and the sample mount is arranged to rotate relative to the enclosure.

In some embodiments, the axis of the relative rotation is perpendicular to a centreline of the beam path.

BRIEF DESCRIPTION OF THE DRAWINGS

To better understand the present invention, and to show how the same may be carried into effect, reference will be made, by way of example only, to the accompanying Drawings, in which.

DETAILED DESCRIPTION

Figure 6:
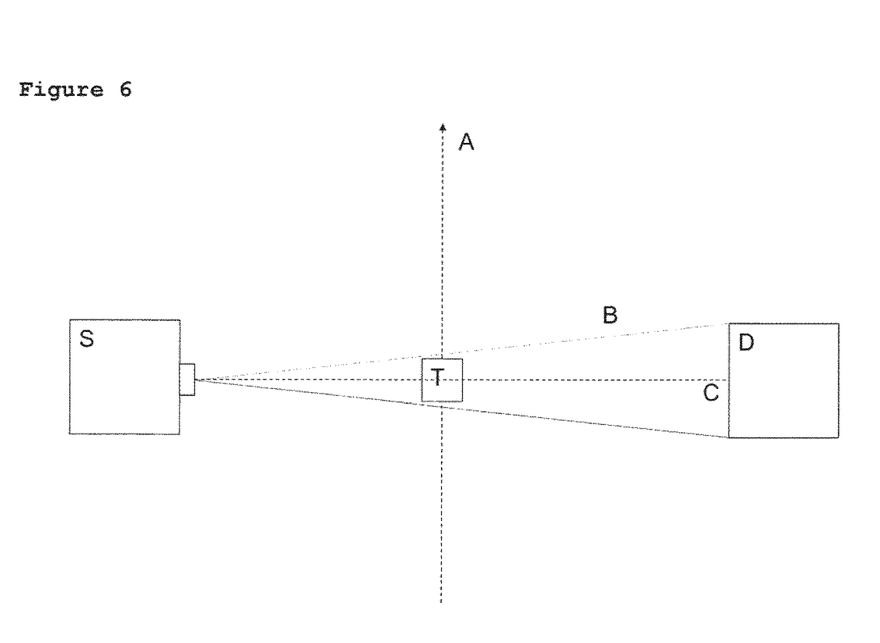
FIG. 6 shows a typical configuration of source, detector and sample for x-ray computed tomography suitable for use in implementing the present disclosure.

The basic concept of computed tomography is shown in FIG. 6. FIG. 6 shows a source of x-ray radiation S and a detector D for the radiation. The source S emits a beam B of the radiation which is detected at detector D. Interposed between source S and detector D is a target object T, the internal structure of which is intended to be analysed. This arrangement is common to both traditional and CT imaging.

In computed tomography, the target object T is relatively rotated around axis A with respect to a reference frame defined by source S, detector D, and beam B. Beam B has a centreline C. At small angular intervals of rotation, a sequence of radiographic projections is acquired by detector D. After a complete circular rotation about axis A, the sequence of images so obtained are synthesized into a volume map of object T in terms of the relative opacity of target object T to the selected radiation. While it is conventional to use a complete 360 degree rotation to obtain the sequence of images, in some cases it is acceptable to acquire images covering a rotation angle of at least 180 degrees.

Such a volume map can be used to determine the internal structure of target object T. The mathematical techniques used to transform the series of individual radiographic images, or radiographic projections as they are conventionally termed, into the volume map form part of the common general knowledge of one skilled in the art in this field, and are normally computerised or computer-implemented.

Depending on the type, and especially on the size, of target object T, the fixed reference frame for the rotation about axis A can be selected. In some cases, the source and detector can in opposition rotate about the axis A, for example in medical imaging applications where it is impractical to rotate a human body or body part as a whole. In other cases, when target object T is small, the object may be placed on a turntable and can be rotated about axis A while using a fixed source S and fixed detector D. This latter scenario is usual in industrial CT imaging.

Figure 1:
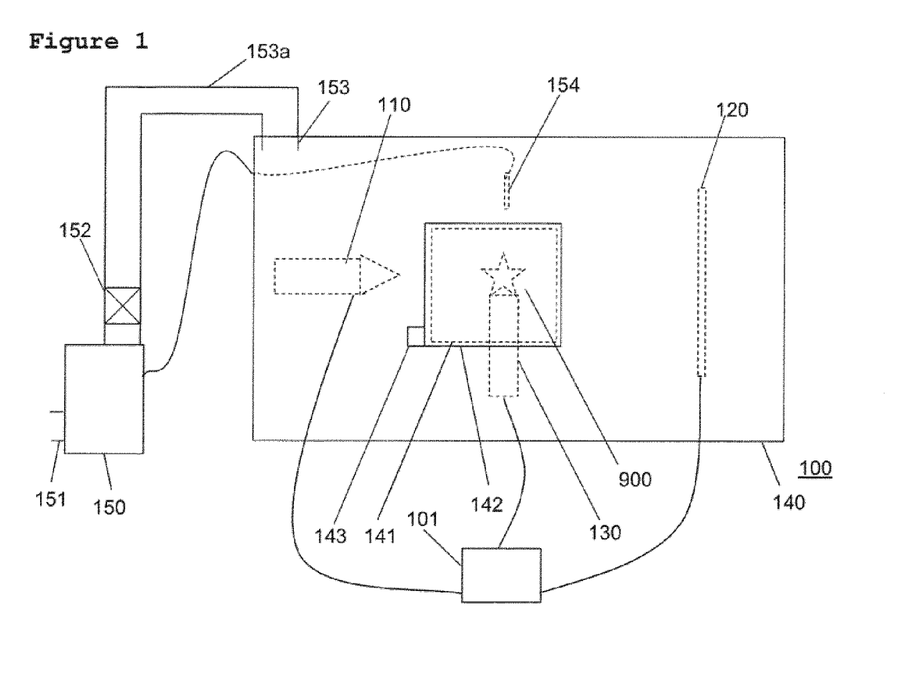
FIG. 1 shows a first embodiment of an x-ray imaging system according to the present disclosure.

FIG. 1 shows a first embodiment 100 of an x-ray imaging system. System 100 comprises x-ray source 110, which is adapted to generate x-rays of a particular energy profile and to direct them in a beam propagating along a beam centreline. For example, x-ray source 110 can produce x-rays of around 100 keV and can direct them in a conical beam with angular divergence of approximately 10 degrees about the beam centreline. Opposed to x-ray source 110 along the beam centreline is detector 120, which is arranged to receive the x-ray beam originating from source 110.

Detector 120 is here a two-dimensional pixel array detector, having a grid of pixel regions each of which is adapted to measure the intensity of x-rays arriving at the detector during a predetermined exposure interval. While historically x-ray detectors have included a plate coated in x-ray sensitive photographic emulsion, in modern systems, including computer tomography (CT) systems, it is conventional for such detectors to be electronic. For example, the pixel regions of detector 120 may each be charge-coupled devices (CCDs) sensitive to the energy of x-rays provided from source 110.

Figure 4:
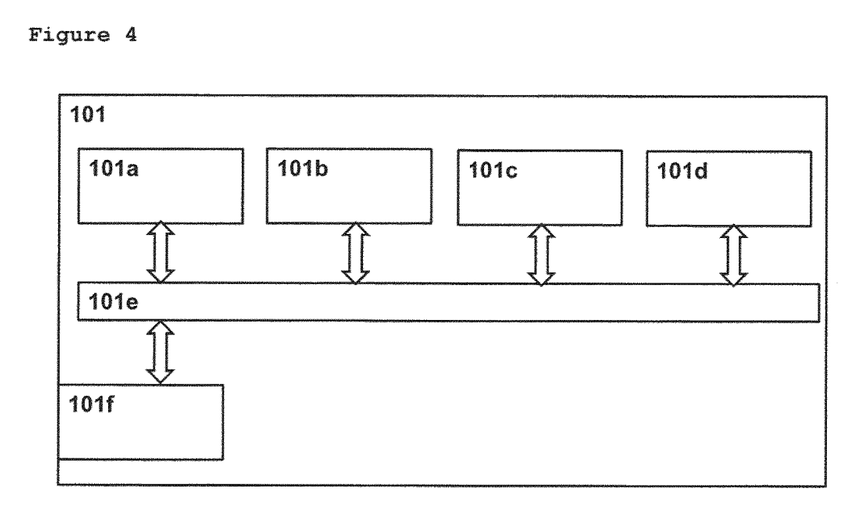
FIG. 4 shows a control computer suitable for implementing the present disclosure.

Preferably, source 110 and detector 120 are arranged to communicate with a control computer 101, shown in more detail in FIG. 4, which functions as a system controller to control the x-ray emission from source 110, to record the intensity data obtained from detector 120 and, optionally, to perform the computed tomography reconstruction. Detector 120 is appropriately sized so that the beam of x-rays from source 110 is recorded over a particular angular range either side of the beam centreline, which may or may not be the full angular divergence of the beam. Although the beam from source 110 may have circular or elliptical s etry about the beam centreline, detector 120 is usually square or rectangular for ease of manufacture. Therefore, it is usual for the angular divergence of the beam from source 110 and the dimensions of detector 120, as well as the spacing between source 110 and detector 120 to be selected such that the beam completely fills detector 120.

To acquire an image of a sample, the sample is interposed in the beam path between source 110 and detector 120. Preferably, for high-resolution imaging, the sample should be placed and positioned on the beam centreline so that the projected image of a region of interest of the sample on the detector just fills the pixel grid of the detector in order to make full use of the available resolution of the detector. Therefore, to accurately position the sample, a sample mount 130 is provided which provides a platform or other support structure on which a sample, shown in FIG. 1 as sample 900, may be positioned. Typically, the platform or other support structure on which the sample is positioned is made of a radiolucent material, so that elements of the sample mount which are in the beam path do not appear in the acquired image.

Sample mount 130 may be a single fixed mount point, or may be adjustable for translation of the sample in one or more directions along and across the beam path, and for rotation of the sample about one or more rotation axes, to allow for proper positioning of the sample in the beam path. In the embodiment of FIG. 1, sample mount 130 allows translation of the sample 900 in three axes, being one axis along the beam path and two axes across the beam path, and also allows rotation of the sample about a single axis which crosses the beam path perpendicular to a centreline of the beam path. In the embodiment of FIG. 1, rotation of the sample 900 by sample mount 130 is used in the acquisition of the series of projections at different angles required for the computed tomography reconstruction. However, in other embodiments, rotation of the source-detector system, about a predetermined axis passing through the sample mount may be used to obtain the series of projections, or rotation of the entire sample mount 130 by a separate rotation stage, may be used for the series acquisition.

As shown in FIG. 4, control computer 101 here includes a rotation controller 101a which is adapted to control the relative rotation of source and detector with reference to the sample mount. For example, rotation controller may be provided as a software or hardware unit which gives rotation commands to sample mount 130.

Control computer 101 also comprises a memory 101b adapted to record a series of x-ray images acquired at a series of angles in the relative rotation of source and detector with reference to the sample mount. Memory 101b may be, for example, implemented as a solid state store or hard disk drive, and may also be adapted to record rotation data obtained from rotation controller 101b which corresponds the rotation commands given to sample mount 130.

Control computer 101 also comprises a tomography reconstruction unit 101c, which is adapted to apply mathematical transformations to the series of x-ray images, optionally also with reference to the acquired rotation data, to calculate a volumetric density map. Mathematical transforms suitable for x-ray tomographic reconstruction are known in the art, and may be selected based on factors including the quality of the reconstruction required and the processing power available.

Control computer 101 also comprises a source controller 101d, which is adapted to control the functions of source 110, for example to initiate and terminate production of x-rays and to adjust beam parameters including beam divergence, x-ray flux and x-ray energy.

Control computer 101 has a communications bus 101e, which communicates between units 101a, 101b, 101c and 101d. Communications bus 101e also communicates with interface module 101f, by means of which units 101a, 101b, and 101d at least, are able to communicate with, respectively and for example, sample mount 130, detector 120, and source 130. Interface module 101f may be, for example, a General Purpose Interface Bus (GPIB) interface, a USB (Universal Serial Bus) interface, or an Ethernet interface.

Control computer 101 may be, for example, a microprocessor having software modules adapted to perform each of its functions. Alternatively, control computer 101 may be provided as a distributed control and processing network, having discrete hardware modules adapted to perform each of its functions, and communicating via a network. Further, control computer 101 may be implemented as a group of discrete industrial controllers which are configured to communicate with each other via communications channels, such as RS232 communications links.

Source 110, detector 120, and sample mount 130 are each provided within, that is, at an interior of, enclosure 140, one of the functions of which is to prevent x-rays generated, scattered or reflected within the enclosure from exiting the enclosure, and another of the functions of which is to prevent any undesired objects from crossing the beam path or interfering with the sample, source or detector during the imaging process. While enclosure 140 may take a variety of forms, for simplicity enclosure 140 can be considered to be a cuboidal box having a layer or sheet of radiodense material, such as lead or lead alloy, applied to each surface to form a radiopaque barrier preventing the leakage of x-ray radiation from the enclosure.

To allow an operator to exchange samples, and to allow the position of sample 900 on sample mount 130 to be adjusted, enclosure 140 has an aperture 141 in one external surface of the enclosure which connects the exterior and the interior of the enclosure. The aperture is sufficiently large to allow an operator to easily exchange or position samples. The chosen size of aperture 141 will depend on the maximum size of the sample which must be introduced through it, and will also depend on the access requirements for the hands of the operator or for suitable implements to be introduced through the aperture to adjust the sample.

For example, for large samples, special handling equipment such as cranes may be required to introduce and remove samples, while for very small samples, tweezers or tongs may be used to introduce and remove the sample. However, for samples which are suitable for straightforward manual handling, it is envisaged that an aperture having an area of around 1 m$^2$, preferably less than 1 m$^2$, and having an approximately square shape will be appropriate. For certain applications, such as room-sized enclosures, an aperture larger than 1 m$^2$ may be provided to allow large samples to be imaged and even to allow the operator to enter the enclosure and perform necessary tasks.

To prevent the undesired emission of x-rays from source 110 through aperture 141, for example during the acquisition process, and to avoid disturbance of the sample or the source-detector system during the acquisition process, aperture 141 is provided with a door 142, which also includes a layer of radiodense material, and which is sized either to fit the aperture in the manner of a plug or to be slightly larger than the aperture and to cover the aperture when closed. For example, the door may be hinged, and may be opened by an operator to access the sample space. Alternatives to a hinged door include a removable door or a sliding door.

In the embodiment of FIG. 1, for reasons of safety, an interlocking mechanism is provided which disables the operation of the x-ray source 110 when the door is opened. Here, such interlocking is provided by door sensor 143, which detects whether or not door 142 is closed, and communicates with x-ray source 110 to only permit operation of the source 110 when the door is closed. Door sensor 143 may, for example, be a switch which is closed when the door is closed, or may be a non-contact sensor such as an optical sensor which exhibits a change in an electrical property, such as conductivity, when the door is closed. Such communication can occur via, for example, control computer 101.

The operation of the x-ray imaging components, especially source 110, generates a certain amount of heat, which tends to raise the temperature inside enclosure 140. Conduction of heat through enclosure 140 from interior to exterior will tend to balance the generation of heat by the imaging components. Therefore, when the door is closed and the system is operating, the temperature will tend to an equilibrium value.

In contrast, when the door is opened, there is the potential for air from outside the enclosure to mix with air inside the enclosure in sufficient quantity as to cause a sudden change in temperature inside the enclosure. If allowed to occur, this may cause dimensional instability in one or more of sample 900, source 110 and detector 120.

To avoid such a temperature change, a climate control system including air conditioner 150 is provided to supply air with a predetermined temperature to the interior of enclosure 140. Air conditioner 150 draws air, for example by means of a blower, through inlet 151, which is located outside enclosure 140. Air conditioner 150 then adjusts the temperature of the air, for example, by means of one or more of a heat exchanger, a cooler and a heater acting as a temperature regulator, to a temperature approximately equal to a normal operating temperature inside the enclosure, and then supplies the air via flow regulator 152, being, for example, a valve, and via conduit 153$a$ and outlet 153 to the interior of the enclosure. In so doing, the air conditioner generates an overpressure inside enclosure 140 relative to the pressure outside enclosure 140, namely, a positive pressure differential between the interior and the exterior of the enclosure.

Figure 5:
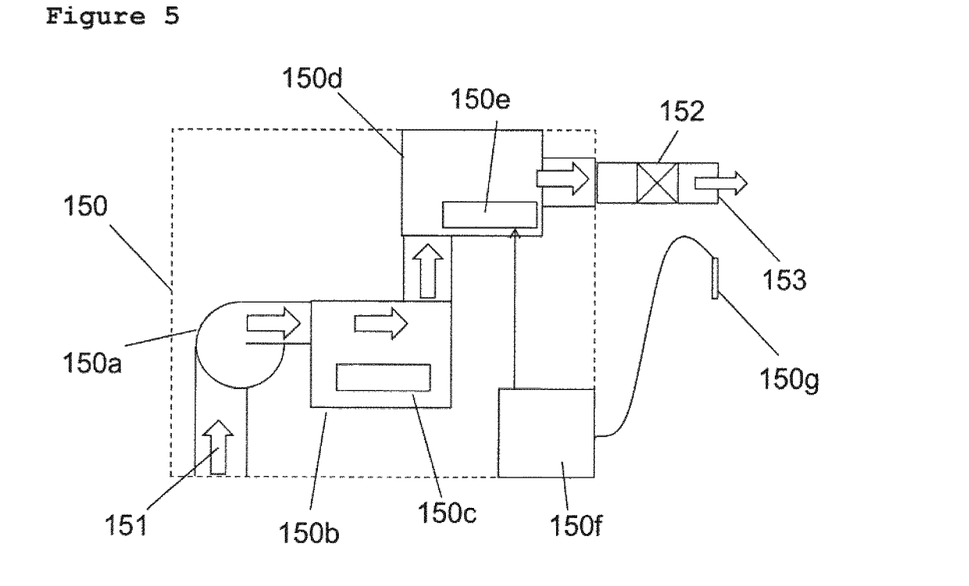
FIG. 5 shows an air conditioner suitable for implementing the present disclosure.

An exemplary construction of air conditioner 150 is shown in FIG. 5. Air conditioner 150 has inlet 151, through which air may be drawn by the action of blower 150$a$. From blower 150$a$, air passes to air cooling unit 150$b$, in which it may be cooled by the operation of cooling element 150$c$. Cooling element 150$c$ may be implemented as, for example, a heat-exchange refrigerator coil in which a cold refrigerant flows. Alternatively, cooling element 150$c$ may be implemented as, for example, a thermoelectric cooling element, such as a Peltier cooler. From air cooling unit 150$b$, air passes to air heating unit 150$d$, in which it may be heated by the operation of heating element 150$e$. Heating element 150$e$ may be implemented as a heat-exchange heating coil in which a hot heat transfer medium flows. Alternatively, heating element 150$e$ may be implemented as, for example, a thermoelectric heating element, such as a coil of resistive wire.

Together, air cooling unit 150$b$ and air heating unit 150$d$ act as a temperature regulator. From air heating unit 150$d$, air passes to regulator 152, which may be implemented as a valve, before passing into enclosure 140 via outlet 153.

Air conditioner 150 has a temperature controller 150$f$, which communicates with outlet temperature sensor 150$g$. Outlet temperature sensor 150$g$ is arranged in or near outlet 153 to measure the outlet air temperature. Temperature controller 150$f$ sends commands to heating element 150$e$ and/or cooling element 150$c$ to vary the heating or cooling action to achieve an intended outlet temperature. The action of temperature controller 150$f$ can be achieved by means of feedback control, for example, by means of a PID (Proportional-Integral-Derivative) controller. However, in other embodiments, outlet temperature sensor may be omitted, and external demands to the air conditioner for cooler or warmer air can be applied to one or both of the heating element 150e and cooling element 150c.

The flow of air obtainable from air conditioner 150 is sufficient so that, even when door 142 is opened, an overpressure inside enclosure 140 may be maintained so as to prevent air from outside the enclosure from entering the enclosure and mixing with the air in the enclosure. Therefore, a significant drop in temperature inside the enclosure may be avoided. Since the enclosure may be maintained at an overpressure even when the door is open, the temperature variations that can cause dimensional instability in the source-detector system, for example changes in the separation or alignment between the source and the detector, or in the sample, are avoided. Therefore, when the door is subsequently closed, the temperature inside enclosure 140 remains approximately equal to the temperature inside the enclosure before the door was opened, and imaging may be almost immediately resumed without the necessity of waiting for the temperature to equilibrate.

Without being bound by any particular theory of operation of the present disclosure, the turbulent volumetric flow Q of air through an aperture of area A is given by the equation $$Q = C_d \cdot A \cdot (2 \cdot \Delta P/\rho)^{0.5}$$

in which $\Delta P$ is the pressure difference across the aperture, $\rho$ is the density of the air, and $C_d$ is a discharge coefficient which is 0.61 for a flat plate aperture, such as a rectangular window. The exponent of 0.5 is selected for turbulent flow, and will vary for laminar or viscous flow conditions associated with very large or very small openings.

Therefore, if air conditioner 150 is capable of providing a volume flow of air to the interior of enclosure 140 exceeding that passing through aperture 141 according to the above equation, the pressure difference will be maintained and the positive differential pressure inside enclosure 140 will exist even when door 142 is open. Conversely, for a desired positive differential pressure through aperture 141, the required volumetric flow provided by air conditioner 150 may be calculated by the above equation. Also, or alternatively, these parameters may be selected by suitable experiment.

The flow velocity $V_f$ through aperture 141 is given by the relationship $V_f = Q/A$ and is, for air of approximately constant density, only a function of the pressure difference between the interior and the exterior of enclosure 140. If the flow velocity through aperture 141 is selected such that the flow of air out from the enclosure is faster than the thermal diffusion speed of heat into the enclosure, the positive pressure differential across aperture 141 will be able to prevent a change of temperature inside enclosure 140.

The construction and functionality of air conditioner 150 can vary depending on the user requirements. In one variant, the air conditioner 150 is arranged to maintain a continuous overpressure inside enclosure 140 even when the door is closed. The degree of flow regulation provided by valve 152 can be adjusted to select the degree of overpressure achieved. However, since the flow of air from outlet 153 may disturb the sample during the imaging process, in another variant, the air conditioner 150 is only operated to provide the overpressure when the door is opened. In this arrangement, air conditioner 150 can be manually activated by the operator to provide an overpressure just before the door is opened, or the air conditioner 150 can be linked to a sensor such as door sensor 143 used in the safety interlock to trigger the air conditioner to provide the overpressure automatically when the door is opened.

Inlet 151, outlet 153, or both may be provided with an air filter to prevent particles from outside the enclosure being drawn into the enclosure while the air conditioner 150 is operating.

The temperature of the air supplied by air conditioner 150 can either be regulated to a predetermined normal operating temperature of the enclosure, or, as shown in FIG. 1, temperature sensor 154 may be positioned inside the enclosure and arranged to measure the air temperature inside the enclosure to inform the air conditioner 150 of the desired temperature of incoming air through outlet 153, so that air supplied from air conditioner 150 can be brought to a correct temperature before being supplied to the interior of the enclosure. In this way, the air supplied through outlet 153 is at approximately the same temperature as the air already inside the enclosure, so that undesired temperature variation is avoided.

In another variant, temperature sensor 154 can be used to detect when the temperature inside the enclosure has changed by more than a predetermined permitted amount from a normal operating temperature. When such a change is detected, the air conditioner 150 is arranged so as to supply additional temperature-regulated air through outlet 153, or air at an increased or decreased temperature, or both, to restore the temperature inside the enclosure to the approximate nominal operating temperature and to provide the overpressure. In such a configuration, temperature sensor 154 can provide feedback control, for example to flow regulator 152 or to the temperature regulator of air conditioner 150, to regulate the amount or temperature of temperature-regulated air provided to the interior of enclosure 140, and thereby to regulate the temperature inside the enclosure. Feedback control can be achieved, for example, by the use of a PID (Proportional-Integral-Derivative) controller. In other embodiments, the air conditioner can be arranged to supply air at a constant predetermined temperature, at a constant predetermined flow rate, or both.

Temperature sensor 154 can include a plurality of temperature sensors provided inside the enclosure, each of which is arranged to provide a local interior temperature measurement at one location in the enclosure. Using such a plurality of sensors allows the climate control system to determine an interior temperature measurement representing the temperature inside the enclosure on the basis of the local interior temperature measurements, for example on the basis of a mean temperature, a modal temperature, a maximum or a minimum temperature in the enclosure as detected by the plurality of temperature sensors.

In the embodiment of FIG. 1, the air conditioner may be adjusted to provide a minimum, or a maximum, or both a minimum and a maximum positive differential pressure between the interior and the exterior of enclosure 140. Such a pressure differential may be selected to be in the range of 1 mbar to 10 mbar when the door is open. The flow of air provided by air conditioner 150 from outlet 153 may be chosen to achieve the required pressure differential when the door is open. Naturally, a larger aperture 141 will require a larger air flow from air conditioner 150 to provide and maintain the positive overpressure when the door is open. However, this will be easily within the capability of one skilled in the art to determine, by means of straightforward experimentation.

Figure 2:
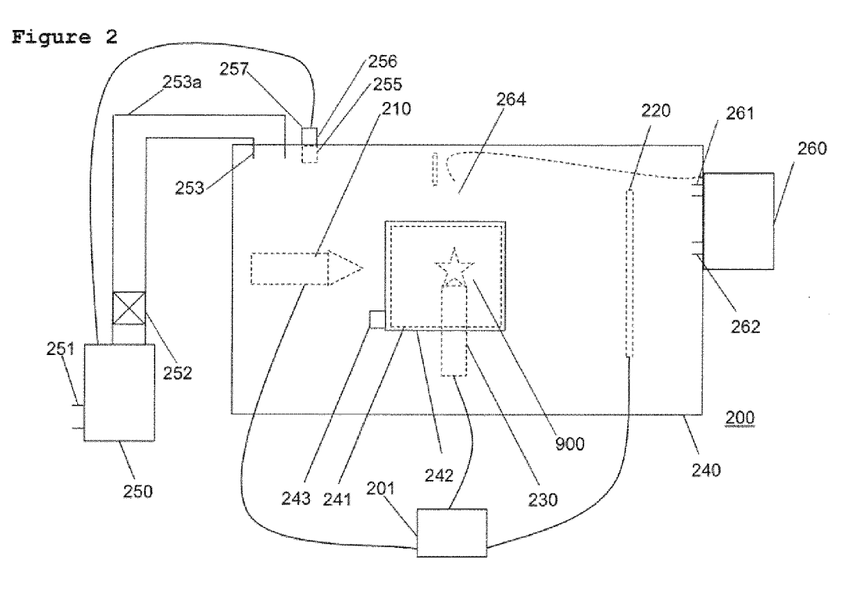
FIG. 2 shows a second embodiment of an x-ray imaging system according to the present disclosure.

In an alternative embodiment, shown in FIG. 2, an additional air conditioner is present which is operable to control the environment, and particularly the temperature, within the enclosure even when the door is closed. With reference to FIG. 2, system 200 exhibits similar elements to system 100 shown in FIG. 1, and similar elements having reference numerals of the form 2xx should be taken to be essentially similar to the elements assigned reference numerals 1xx and described above with reference to FIG. 1. For example, source 210 is essentially similar to source 110, and detector 220 is essentially similar to detector 120 as described above.

In addition to air conditioner 250, which draws air from outside enclosure 240 through inlet 251 from outside the enclosure, regulates its temperature, and provides it via flow regulator 252 through outlet 253 to the interior of enclosure 240 to provide an overpressure even when the door is open, the climate control system of enclosure 240 also comprises secondary air conditioner 260. Secondary air conditioner 260 is a closed-loop air conditioner which has an inlet 261 and an outlet 262 both arranged inside enclosure 240, and is arranged to adjust the temperature by means of a temperature regulator and, optionally, the humidity by means of a humidity regulator, of air passing from inlet 261 to outlet 262. Thereby, secondary air conditioner 260 is arranged regulate the environmental conditions inside enclosure 240, for example, to remove some of the excess heat generated by source 210 when operating to produce x-rays. To this end, secondary air conditioner 260 communicates with a temperature sensor 264 provided inside enclosure 240 to detect the temperature inside the enclosure, and is arranged to adjust the temperature of the air provided from outlet 262 to maintain the temperature detected by temperature sensor 264 at a constant, predetermined level.

In contrast to air conditioner 260, which is not present in the embodiment described with reference to FIG. 1, the operation of air conditioner 250 in the embodiment of FIG. 2 is similar to the operation of air conditioner 150 shown in FIG. 1. In the embodiment of FIG. 2, air conditioner 250 can be configured to operate when the door is open, either as manually activated by an operator or through use of door sensor 243, or air conditioner 250 can continually supply air to the interior of enclosure 240 to maintain a desired overpressure even when door 242 is closed.

Since secondary air conditioner 260 is provided to regulate the temperature of the air inside the enclosure when the door is closed, temperature regulation provided by air conditioner 250 need not be as precise, since if the temperature of air supplied through outlet 253 to provide the overpressure is cooler or warmer than the desired operating temperature inside enclosure 240, feedback from temperature sensor 264 to secondary air conditioner 260 will still enable the overall temperature to be maintained in a stable fashion. However, in some embodiments, it may be preferable that the air conditioner 250 is provided with its own temperature sensor inside enclosure 240, in a similar manner as shown in FIG. 1, to enable the air supplied through outlet 253 to provide the overpressure to have a regulated temperature approximately equal to the temperature already existing within enclosure 240.

Alternatively or additionally, a communication channel can be provided between air conditioner 250 and secondary air conditioner 260, for example using a simple two-wire analogue signal, to communicate temperature information detected by temperature sensor 264, to ensure that the air provided through outlet 253 is at an appropriate temperature for maintaining a predetermined stable temperature inside enclosure 240, for example, is supplied at the same temperature as the air supplied by air conditioner 260. In some circumstances, if secondary air conditioner 260 determines that the temperature inside the enclosure as registered by temperature sensor 264 has deviated beyond an acceptable, predetermined margin from the desired temperature inside enclosure 240, for example due to the door 242 having been opened for an extended period of time, secondary air conditioner 260 can communicate to air conditioner 250 that air at an elevated temperature or a reduced temperature should be provided through outlet 253 to assist in warming or cooling the interior of enclosure 240.

While the secondary air-conditioning system 260 is able to regulate the air temperature inside the enclosure while it is closed, it may be impractical or expensive to provide a conventional air-conditioning system alone which is powerful enough to maintain the temperature within the enclosure when the enclosure is open. Furthermore, it may be also impractical or expensive to maintain the whole environment in which the enclosure may be situated, and within which the operator may work, at the same temperature as that inside the enclosure. Especially, an appropriate ambient operating air temperature for the components inside the enclosure may be very different from a preferred environmental temperature for the operator outside the enclosure. However, the described combination of air conditioner 250 and secondary air conditioner 260 is especially able to maintain a preferred operating air temperature inside the enclosure both when the enclosure is open and when the enclosure is closed, in a cost-effective and efficient manner.

The embodiment of FIG. 2 also has a differential pressure sensor 257, which comprises exterior pressure sensor 256 and interior pressure sensor 255. Differential pressure sensor 257 communicates with air conditioner 250, and particularly communicates to air conditioner 250 the pressure differential between the interior of enclosure 240 and the exterior of enclosure 240. Preferably, the differential pressure sensor is located at aperture 241, to determine the pressure differential existing near aperture 241 inside and outside enclosure 240. Air conditioner 250 is configured to use the differential pressure reported by differential pressure sensor 257 to determine the quantity of air that should be provided through outlet 253 to the interior of enclosure 240 to achieve or sustain a desired, predetermined pressure differential. For example, differential pressure sensor 257 can be used to feedback to flow regulator 252 the achieved differential pressure, such that flow regulator 252 will permit greater flow into the enclosure the further the measured differential pressure by differential pressure sensor 257 is from a predetermined desired differential pressure.

Such an arrangement can also be used with the single air conditioner configuration shown in FIG. 1, by providing a differential pressure sensor to air conditioner 150. In alternative embodiments, only the exterior pressure sensor 256 or the interior pressure sensor 255 may be provided. If only interior pressure sensor 255 is provided, then the exterior pressure may be assumed to be normal atmospheric pressure, while if only exterior pressure sensor 256 is provided, a model of enclosure 240 may be used, together with information provided by flow regulator 252 on the rate of air supplied to enclosure 240, to estimate the internal pressure. For this purpose, information about the temperature inside enclosure 240 obtained from temperature sensor 264 may be used, also.

In some embodiments air conditioner 150/250 may be provided having two flow settings of the flow regulator, a first, smaller flow setting for generating a desired overpressure when the door is closed and a second, larger flow setting for generating the approximately the same desired overpressure when the door is open. Such arrangements are able to prevent a large pressure change when the door is opened, which pressure changes may also be associated with temperature changes of the air inside the enclosure.

In any of the described embodiments, to improve the capability of enclosure 140 or enclosure 240 to maintain the internal temperature even when door 142 is open, aperture 141 may additionally be provided with a curtain for restricting the flow of air through the aperture even when the door is open.

Figure 3A:
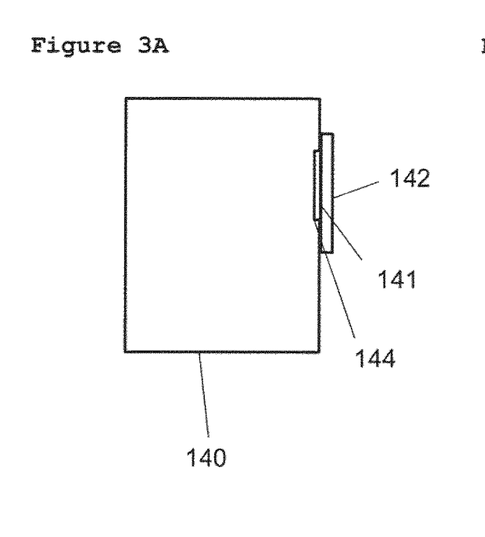
FIG. 3a shows a cross-section of a variant embodiment of an x-ray imaging system of the present disclosure.

For example, as shown in FIG. 3a, a flexible curtain 144 may be provided to cover aperture 141 to provide a physical barrier to the flow of air from outside enclosure 140 to the interior of enclosure 140 via aperture 141. For example, curtain 144 can be formed by a series of strips of material, such as polymer material, extending, or hanging, across the height and width of aperture 141. For example, transparent vinyl strips may be used, or for increased radiation safety, lead-doped vinyl strips may be used.

Figure 3B:
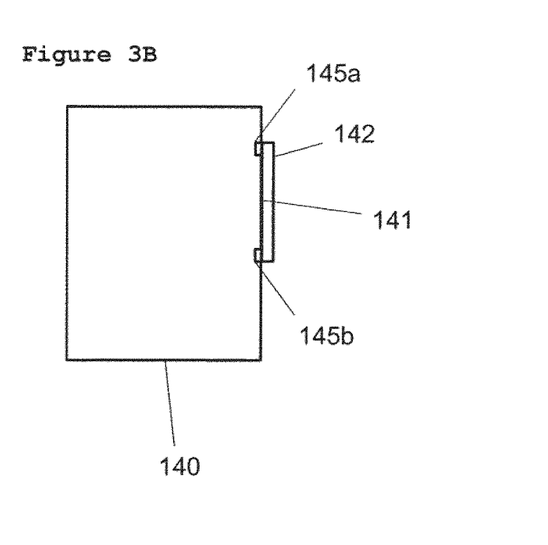
FIG. 3b shows a cross-section of a further variant embodiment of an x-ray imaging system of the present disclosure.

In alternative variant, as shown in FIG. 3b, an air curtain may be provided to provide a directional air stream across the entire height and width of aperture 141 to reduce to infiltration of air from the exterior of the enclosure 140 to the interior. The air curtain is provided by air curtain discharge nozzle 145a, which is arranged to direct a flow of air across the height and width of the opening. In the embodiment shown in FIG. 3b, air curtain recovery nozzle 145b is provided opposed to air curtain supply nozzle 145a across the height of aperture 141 to provide a suction to control turbulence in the air curtain supplied by discharge nozzle 145a. However, air curtain recovery nozzle 145b is optional, and a relatively uniform flow of air across aperture 141 may be obtained in some circumstances with the use of air curtain discharge nozzle 145a alone.

In any of the above variants, although the length of conduit 153a/253a from regulator 152/252 to outlet 153/253 is shown as a long section of conduit, it is also possible to arrange regulator 152/252 in a short section of conduit between air conditioner 150/250 and outlet 153/253> However, it may be preferred that the total path from inlet 151/251 to outlet 153/253, and preferably, the total path between air conditioner 150/250 and outlet 153/253 is relatively long compared with the cross-sectional dimensions of the conduit.

In each of the above variants, the degree of overpressure achieved inside the enclosure is determined by the flow regulator 152/252. However, if a simple blower, such as a centrifugal blower, is used as part of air conditioner 150/250 to draw air from inlet 151/251 and supply it to outlet 153/253, the efficiency of the blower will decrease as pressure rises in enclosure 140/240. Accordingly, in some operating circumstances, a simple blower will self-regulate to provide the desired degree of overpressure. In such cases, one skilled in the art will be able to select a blower having suitable back-pressure flow characteristics to ensure that an appropriate overpressure will be achieved, even when door 142/242 is open. However, in other embodiments, feedback, such as by a differential pressure sensor, is used to actively regulate the flow of air, whether by adjusting a flow regulator or simply by adjusting the operating speed of the blower of air conditioner 150/250, to achieve a predetermined degree of overpressure. A combination of both methods may also be used.

In the above embodiments, it is assumed that the enclosure encloses all of the source, the detector and the sample mount. However, an alternative arrangement is possible, in which the sample mount is contained within a sample chamber, defined by an enclosure and having a closable aperture, and at least one or both of the source and detector are provided outside the sample chamber. In such an arrangement, the x-rays may be introduced to the sample chamber from the source and/or allowed to exit the sample chamber to the detector through one or more appropriately positioned x-ray transparent windows. In such an arrangement, heat generated outside the sample chamber, for example by the source or detector, may have less impact on the temperature inside the sample chamber than if the source and/or detector were enclosed by the same enclosure as the sample. However, temperature fluctuations caused by opening the door may still affect the dimensional stability of the sample. Therefore, the arrangements described above for improving the temperature stability inside an enclosure are also applicable. For safety, such arrangements may also require a secondary enclosure to surround the source and the detector, or the source and the detector may be configured such that, when properly aligned with the windows of the sample chamber, undesired leakage of x-rays will not occur. Therefore, in each of the described embodiments, either the source, the detector, or both may be located outside the enclosure, without limitation.

Although the present disclosure has been described with reference to computed tomography 3D imaging systems, the concepts disclosed herein may also be applied equivalently to 2D x-ray imaging systems.

The above-described embodiments, taken together or separately, should be understood to be purely exemplary, and one skilled in the art will be able to modify or adapt the described embodiments and to apply the disclosed concepts to suit local preferences and engineering requirements. Accordingly, the scope of the present invention should be understood as being limited only by the scope of the appended claims, which should be taken to encompass all modifications, adaptations, or substitutions which one skilled in the art could achieve in light of the technical concepts presented in the foregoing disclosure.

The invention claimed is:

1. A computed tomography (CT) x-ray imaging apparatus, comprising:
    an x-ray source;
    an x-ray detector;
    a sample mount for mounting a sample in a beam path between the x-ray source and the x-ray detector;
    an enclosure enclosing at least the sample mount in an interior of the enclosure; and
    a climate control system for regulating the climate inside the enclosure, wherein:
    the enclosure has an aperture for enabling access to at least the sample mount from outside the enclosure;
    the enclosure is provided with a door operable between an open position in which the aperture is open and a closed position in which the aperture is closed by the door; and
    the climate control system is operable to provide a positive pressure differential between the interior of the enclosure and an exterior of the enclosure such that the interior of the enclosure is maintained at a higher pressure than the exterior of the enclosure when the door is open.

2. The CT x-ray imaging apparatus of claim 1, wherein the climate control system is configured to detect a condition in which the door is open and to provide the positive pressure differential when the door is open.

3. The CT x-ray imaging apparatus of claim 1, wherein the climate control system comprises at least one temperature sensor inside the enclosure and arranged to provide an interior temperature measurement.

4. The CT x-ray imaging apparatus of claim 3, wherein the climate control system comprises a plurality of temperature sensors inside the enclosure each arranged to provide a local interior temperature measurement at one location in the enclosure, and wherein the climate control system is arranged to determine an interior temperature measurement on the basis of the local interior temperature measurements.

5. The CT x-ray imaging apparatus of claim 1, wherein the climate control system comprises a pressure sensor inside the enclosure and arranged to provide an interior pressure measurement.

6. The CT x-ray imaging apparatus of claim 1, wherein the climate control system comprises a pressure sensor outside the enclosure and arranged to provide an exterior pressure measurement.

7. The CT x-ray imaging apparatus of claim 1, wherein the climate control system comprises a differential pressure sensor arranged to provide a differential pressure measurement between the interior and the exterior of the enclosure.

8. The CT x-ray imaging apparatus of claim 1, wherein the climate control system comprises an air conditioner arranged to regulate at least the temperature of the air inside the enclosure.

9. The CT x-ray imaging apparatus of claim 1, wherein the climate control system comprises a blower arranged to draw air from outside the enclosure and to supply it to the interior of the enclosure to provide the positive pressure differential.

10. The CT x-ray imaging apparatus of claim 9, wherein the air conditioner comprises a temperature regulator for regulating the temperature of the air supplied from outside the enclosure to the interior of the enclosure.

11. The CT x-ray imaging apparatus of claim 9, wherein the climate control system comprises an air flow regulator for regulating the flow of the air supplied by the blower from outside the enclosure to the interior of the enclosure.

12. The CT x-ray imaging apparatus of claim 10, wherein the temperature regulator comprises a further air conditioner arranged to regulate the temperature inside the enclosure.

13. The CT x-ray imaging apparatus of claim 1, wherein the climate control system is configured to detect a condition when a temperature inside the enclosure either exceeds or drops below a predetermined threshold and to provide the positive pressure differential when the temperature exceeds or drops below the predetermined threshold.

14. The CT x-ray imaging apparatus of claim 1, wherein the climate control system is configured to detect a condition when a temperature inside the enclosure either exceeds or drops below a predetermined threshold and to adjust the temperature of the air supplied from outside the enclosure to the interior of the enclosure when the temperature exceeds or drops below the predetermined threshold.

15. The CT x-ray imaging apparatus of claim 1, wherein the enclosure comprises a flexible curtain arranged to cover the aperture when the door is open.

16. The CT x-ray imaging apparatus of claim 15, wherein the curtain is transparent.

17. The CT x-ray imaging apparatus of claim 1, wherein the enclosure comprises an air curtain arranged to operate across the aperture to reduce air flow through the aperture when the door is open.

18. The CT x-ray imaging apparatus of claim 17, wherein the air curtain is configured to operate when the door is open.

19. The CT x-ray imaging apparatus of claim 1, wherein the aperture is less than 1 $m^2$ in area.

20. The CT x-ray imaging apparatus of claim 1, wherein the enclosure also encloses the x-ray source, the x-ray detector, or both.

21. The CT x-ray imaging apparatus of any-claim 1, wherein the air conditioner is arranged to provide a positive differential pressure of between 1 and 10 mBar when the door is open.

22. The CT x-ray imaging apparatus of claim 1, wherein the mount, source and detector are together configured for computed tomography imaging such that the source and detector are relatively rotatable with reference to the sample mount.

23. The CT x-ray imaging apparatus of claim 22, wherein the system further comprises a controller adapted to control the relative rotation of the x-ray source and the x-ray detector with reference to the sample mount.

24. The CT x-ray imaging apparatus of claim 22, wherein the apparatus further comprises a memory adapted to record a series of x-ray images acquired at a series of angles in the relative rotation of the x-ray source and the x-ray detector with reference to the sample mount.

25. The CT x-ray imaging apparatus of claim 24, wherein the apparatus further comprises a tomography reconstruction unit, which is adapted to apply mathematical transformations to the series of x-ray images to calculate a volumetric density map.

26. The CT x-ray imaging apparatus of claim 22, wherein the x-ray source and the x-ray detector are arranged to be fixed relative to the enclosure and the sample mount is arranged to rotate relative to the enclosure.

27. The CT x-ray imaging apparatus of claim 22, wherein the axis of the relative rotation is perpendicular to a centreline of the beam path.

* * * * *